United States Patent
Celentano et al.

[11] Patent Number: 5,972,715
[45] Date of Patent: Oct. 26, 1999

[54] USE OF THERMOCHROMIC LIQUID CRYSTALS IN REFLECTOMETRY BASED DIAGNOSTIC METHODS

[75] Inventors: Michael Celentano, Indianapolis; Chris T. Zimmerle, Elkhart, both of Ind.

[73] Assignee: Bayer Corporation, Elkhart, Ind.

[21] Appl. No.: 08/773,269

[22] Filed: Dec. 23, 1996

[51] Int. Cl.[6] .................................................. G01N 21/00
[52] U.S. Cl. .............................. 436/164; 436/46; 436/63; 436/165; 436/169; 422/82.05; 422/82.09; 374/161; 374/162; 435/4; 435/25
[58] Field of Search .......................... 436/46, 63, 164, 436/165, 169; 422/82.05, 82.09; 374/161, 162; 435/4, 25

[56] References Cited

U.S. PATENT DOCUMENTS

| | | | |
|---|---|---|---|
| 4,310,577 | 1/1982 | Davison et al. | 428/1 |
| 5,328,852 | 7/1994 | Blackwood et al. | 436/518 |
| 5,547,283 | 8/1996 | Kronberg | 374/162 |

FOREIGN PATENT DOCUMENTS 0851229  7/1998  European Pat. Off. .

OTHER PUBLICATIONS

Kubo et al "Temperature dependency of optical properties of thermochromic materials". Netsu Bussei (1997), 11(2), 39–45 Abstract only, 1997.

Nagai, Hirotoshi "Indicator for anesthetic gases by means of cholesteric liquid crystal". Fukushima Igaku Zasshi, 30(5/6) 357–64. Abstract only, 1980.

*Primary Examiner*—Jill Warden
*Assistant Examiner*—Sharidan Carrillo
*Attorney, Agent, or Firm*—Jerome L. Jeffers

[57] ABSTRACT

A method for improving the accuracy of temperature sensitive diagnostic assays which are carried out using reflectance spectrometers to detect color changes in a solid test system which has been contacted with a fluid test system suspected of containing an analyte whose presence and/or concentration is being sought. The method involves determining the temperature of the solid test material by measuring the reflectance of a thermochromic liquid crystal in close proximity to the solid test material and correcting the result of the assay for a change in temperature from a pre-selected nominal temperature.

10 Claims, 4 Drawing Sheets

USE OF THERMOCHROMIC LIQUID CRYSTALS IN REFLECTOMETRY BASED DIAGNOSTIC METHODS

BACKGROUND OF THE INVENTION

The present invention is concerned with diagnostic test strips and an improved method for reading them by means of a reflectance spectrometer.

Test strips for the analysis of components in a liquid such as human body fluid are well known. Typically such strips are made of an absorbant material in which there is absorbed a reagent system which responds to the presence of an analyte in the test fluid with a visually detectable signal such as a change in color. This change in color, which appears in one or more test field of the strip, can be the result of an enzymatic reaction in which a redox dye is oxidized or reduced to produce the colored response. Alternatively, the strip is made of a material through which the analyte and labeled antibodies specific therefor can flow to form analyte/labeled antibody conjugates which are captured in a specific detection zone of the strip to provide a detectable response representing the concentration of the analyte in the fluid test sample.

While the detectable response obtained using such strips can be observed visually to obtain a qualitative or semi-quantitative measure of the analyte in the test sample, greater quantitation and faster, more reliable handling of multiple test strips can be realized by instrumentally reading the developed strips. Such instrumental reading is usually accomplished by the use of a reflectance spectrometer which determines the intensity of the reflection from the test field surface. This sort of instrument determines the intensity of the reflected light in the developed strip by illuminating the strip with light at one angle (typically 90°), detecting the reflected light at a different angle (typically 45°) and selecting the measured color or wavelength range at either the source or the detector.

Since the spectrometer is programmed to take the reflectance reading at a particular point in time and the intensity of the visually detectable signal can vary with a change in ambient temperature, because the reaction rate and/or equilibrium are often temperature dependent, there is a need for some means by which temperature variations can be factored out of the assay.

The present invention involves the use of thermochromic liquid crystals in conjunction with the reading of test strips by spectrophotometric means to aid in correcting the readout of the spectrophotometer for variations in ambient temperature. The use of thermochromic liquid crystals (TLCs) in research and testing is becoming increasingly widespread particularly in the areas of flow visualization and heat transfer studies. The TLCs react to changes in temperature by changing color as their name implies. They typically have chiral (twisted) molecular structures and consist of optical mixtures of organic chemicals. The proper name for these materials is cholesteric or chiral nematic liquid crystals. The term cholesteric is historical and is derived from the fact that the first materials to show the characteristic properties and structure of thermochromic liquid crystals were esters of cholesterol. However, many optically active chemicals and mixtures thereof which are not related to cholesterol or other sterols also exhibit the cholesteric liquid crystal structure. TLC mixtures can be divided into 2 distinct types according to their chemical compositions. These types are cholesteric, i.e. formulations comprised entirely of cholesterol and other sterol related chemicals and chiral nematic, i.e. formulations comprised entirely of non-sterol based chemicals. A third category of TLCs arises from the fact that cholesteric and chiral nematic chemicals can be mixed together to provide formulations which exhibit a continuum of physical and chemical properties somewhere between those of their pure cholesteric and pure chiral nematic precursors.

TLCs exhibit colors by selectively reflecting incident white light. Conventional temperature sensitive mixtures turn from colorless (black against black background) to red at a given temperature and, as the temperature increases, pass through the other colors of the visible spectrum in sequence (orange, yellow, green, blue, violet) before turning colorless (black) again at yet higher temperatures. Since the color changes are reversible, the color sequence is reversed upon cooling. TLCs can be used in a number of different forms such as unsealed liquids which are essentially oils with the consistence at their working temperatures being between that of a thin oil and a viscous paste which are applied in thin uniform films, microencapsulated forms in which droplets of the TLC are surrounded by a continuous polymer coating or coated sheets in which a thin film of the liquid crystal is sandwiched between a transparent polymer sheet as substrate and a black absorbing background.

SUMMARY OF THE INVENTION

The present invention involves an improvement to a spectrophotometric test for the presence and/or concentration of an analyte in a fluid test sample when a temperature sensitive assay is employed. This type of assay can be used with any type of system which provides a spectrophotometrically detectable color change upon contacting a solid test material with a fluid sample containing the analyte. The improvement involves detecting the temperature of the solid test material by spectrophotometrically measuring the reflectance of a thermochromic liquid crystal in close proximity to the solid test material. After the temperature is determined, the results of the assay are compensated for any change in temperature from a pre-selected nominal temperature which the test material has undergone.

DESCRIPTION OF THE INVENTION

Figure 1:
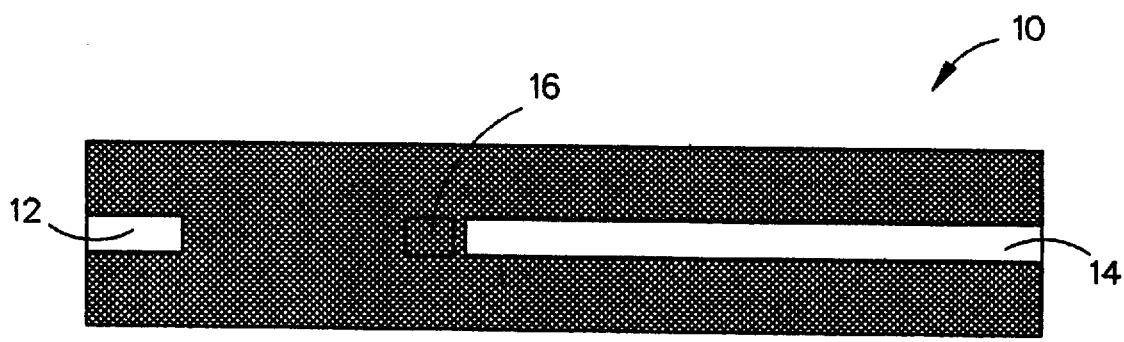
FIG. 1 illustrates a TLC affixed to an instrument table.

The present invention is a means for correcting for changes in ambient temperature pursuant to the spectrophotometric reading of test strips which, when contacted with an analyte in a fluid test sample, provide a spectrophotometricly detectable response. When this response is subject to influence by ambient temperature changes, so that the spectrophotometric reading will be skewed to give inaccurate results, use of the technique of this invention provides a means for factoring out inaccuracies in the reading which can be applied to existing spectrophotometers with only minimal changes to the hardware being required. The technique is applicable to both the traditional colorimetric type of assay strip, in which a redox dye is caused to change color by an enzymatic reaction, or the more recently introduced immunochromatographic strips in which a ligand labeled with a visually detectable marker combines with an analyte to provide a visually detectable response. Both of these techniques, and particularly the later, are quite sensitive to changes in ambient temperature, and, in the absence of some means of correcting for temperature variations, may provide skewed results. One such assay is the test for urobilinogen; abnormally high levels of which in urine can be indicative of hemolytic and hepatic diseases, biliary obstruction and other bile duct dysfunctions. The standard method for detecting urobilinogen in urine employs the Ehrlich reaction which utilizes an aqueous solution of p-dimethylaminobenzenealdehyde or p-diethylaminobenzaldehyde and hydrochloric acid. In the presence of urobilinogen, there is produced a complex with the Ehrlich reagent which exhibits absorption in the visible spectrum. This reaction is particularly sensitive to variations in ambient temperature. In the immunochromatographic type assay, the labeled ligand and/or a binding partner thereof, must flow along a strip of porous support material and bind with an immobilized binding partner to provide a visually detectable signal in a particular zone of the strip which signal is indicative of the analyte's presence and/or concentration in the test fluid. Immunochromatography assays are not always sensitive to temperature in a normal ambient range. However, in certain instances, such as the test for deoxypyridinoline (Dpd) in urine, the Dpd antibodies are quite sensitive to changes in temperature. This temperature sensitivity will vary, depending on the particular analyte being sought, which makes it difficult to predict the temperature sensitivity of Ab-An reactions. With enzymes or other typical chemical reactions, the turnover rate increases approximately 2-fold with every 10° C. rise in temperature due to the increase in the molecular encounter rate with increasing temperature. While there is no turnover for an Ab-An reaction, the encounter rate would normally be expected to increase with temperature. In addition, the Ab and An molecular configuration may undergo numerous changes with temperature variation which would alter the reaction rate.

Increased precision in diagnostic assays conducted with these strips is achievable with careful temperature control. Of course, temperature control can be maintained by conducting the assays in an environmentally controlled testing area. This, however, is not always satisfactory because the backfitting of existing reflectance spectrometers with temperature control devices, such as electronic temperature sensors, would be bulky and, in many cases, cost prohibitive. Such temperature control would also involve the use of heater elements and an enhanced power supply, all of which would increase the bulk and power requirements of the instrument. The presently disclosed invention provides compensation for temperature fluctuations through temperature measurement using thermochromic liquid crystals and compensation for the change in temperature through modification of the spectrophotometer's software.

Temperature sensing is through reflectance measurements of a thermochromic liquid crystal having the appropriate characteristics. Suitable TLCs for use in the present invention undergo a visible color change as a function of temperature. The most suitable color change is an increase or decrease in the TLCs optical reflectance as recorded through one of the filters of a reflectance spectrometer having multiple detectors for identifying reflected light at various wavelengths. All TLCs undergo a color change from Black→Color→Black (assuming a black background which is usually the case). Thus, the instrumental recording of this change must be within some range in the color changing region, which is located in a position which can be scanned by the instrument's readhead. Placement of the TLC could be on the test strip itself in order to coordinate the temperature adjustment with a particular assay and to ensure that the TLC has not been in place longer than its long term stability would suggest. Most conveniently the TLC is placed on the instrument's specimen tray just above the top end of the slot for receiving the test strip as illustrated by FIG. 1. Referring to FIG. 1, the specimen tray 10 which is normally equipped with a white calibration strip 12 and a strip placement insert 14 is also provided with a TLC 16 located just above the top of the insert for strip placement.

The instrument's software is modified to cause the spectrometer to read the liquid crystal and translate its reflected color into a temperature measurement by a predetermined mathematical relationship. For example the reflectance of a TLC material affixed to the table of a CLINITEK® 50 urinalysis instrument is read through the instrument's green and red filters and the reflectance values from each of the filters is combined. This combined numerical value is then used to compute the temperature by using a preestablished relationship between the combined red and green reflectance measurements and the table temperature. The modified software and the thermochromic liquid crystal can be installed by the owners of existing instruments thereby updating them to take advantage of the temperature compensating system of the present invention. The system can, of course, be incorporated into new spectrometers before they are sold. This technique is preferable to adding the feature of temperature compensated chemistry to new or existing reflectometry based medical analyzers. The use of TLCs allows the manufacturer of the analyzer to provide the temperature compensation feature at little additional cost and avoid the use of wire ribbons to the specimen table and/or avoid the need for circuit board modifications. The instruments are updated by simply affixing the TLC to the appropriate location and modifying the software.

Through the use of reflectance measurements of a temperature dependent area or pad (TLC), the measurements are related to temperature and used to correct for temperature dependent reagents where temperature control is not available.

The TLC can be applied to each individual test strip or to the instrument as previously described. A number of variations of normal TLC sheet manufacturing are possible for variations in application. If it is desirable to put the TLC directly on the reagent carrier or on components of the instrument, a TLC slurry can be screen printed directly onto the desired location thereby rendering the positioning of the TLC adaptable to a number of locations, shapes and sizes. For greater precision, a number of TLCs can be placed anywhere on the table or strip to allow a wider temperature range to be tracked for better accuracy in a narrow range. Typically each TLC would have a unique temperature signal. The preferred method is to place a single wide temperature range TLC affixed to a portion of the instrument table between the white calibration chip and the strip placement area as shown in FIG. 1 to most accurately record the temperature of the test strip.

The instrument's software is designed to translate the reflectance and color of the TLC into temperature. The following example mathematically describes how the urobilinogen algorithm values changed as a function of temperature. In this case, the values were linear allowing a delta decode to be computed for each of the analyte levels where delta decode refers to a change in the decode as a function of temperature for each of the analyte levels tested. The delta decode values were looked at in terms of a factor change over a 6° C. difference between 30 and 24° C. The 24° C. level was chosen as the nominal temperature since this is the most common environmental temperature at which the instruments will be used and the factor difference, as plotted in FIG. 7, does not appear to be linear. All other temperatures were normalized to this nominal temperature. As non-linearity would require a more complex equation, the normalization at the middle temperature rather than at one of the extremes results in less of a bias at either one of the temperature extremes.

As indicated by the example, the temperature dependent error in the urobilinogen test was reduced by the temperature correction method of the present invention.

The method of practicing the present invention is further illustrated by the following examples.

EXAMPLE I

Figure 2:
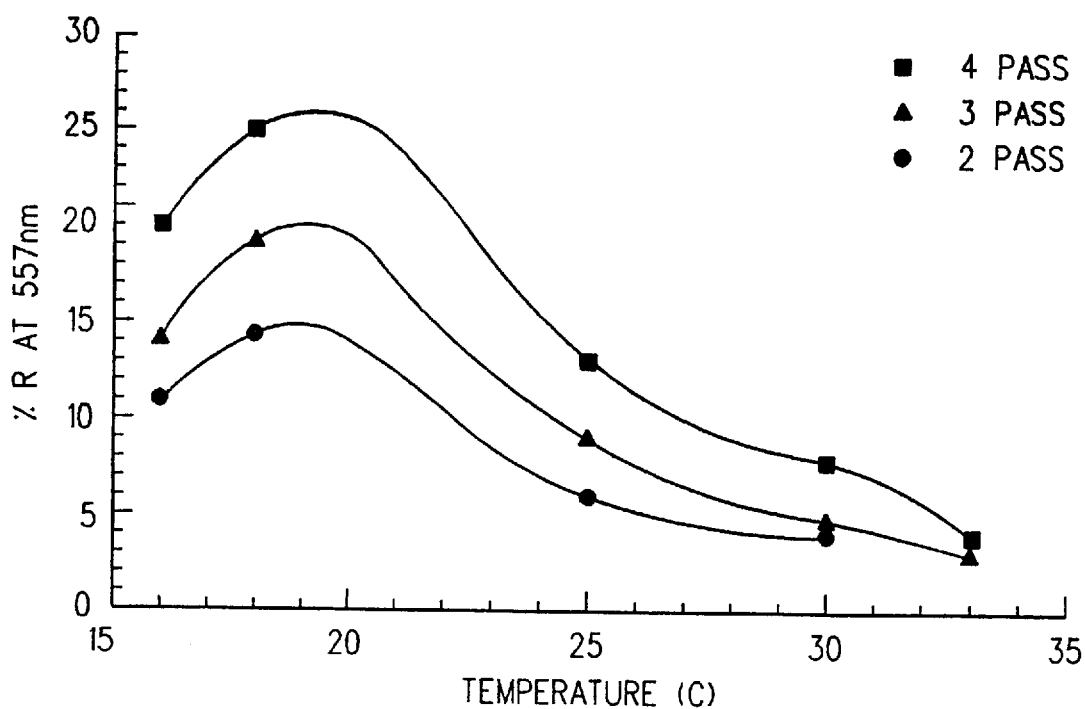
FIG. 2 illustrates changes in reflectance when TLC is applied to a Mylar backing.

Samples of TLC coated onto a Mylar backing with different levels of TLC were obtained from two separate vendors. These were specialized materials made for use in the present invention which are designated here as A and B. The temperature dependence of one of the TLC samples (A) was tested on a CLINITEK® 100 instrument from Bayer Diagnostics using the following procedure:

The TLC was applied to the Mylar backing by multiple passes with a wire rod followed by spreading the material with the rod. The greatest changes in reflectance were noted when the largest amount of TLC (as indicated by the number of passes) was added to the Mylar. This is illustrated by FIG. 2. This illustrates the need for careful quality control to ensure that the thickness of TLC applied to the test strips or instrument remains consistent from strip to strip or instrument to instrument.

The other TLC (B) was tested in a similar manner. The B material gave a response which, while visually more distinct, gave less of a signal difference between thicknesses. The problem with this TLC was that it underwent too large of a color change in the temperature range of interest. It is difficult to deal with reflectance changes which are both increasing and decreasing within a given temperature region. Although the A material showed less visible change, the fact that the reflectance would only decrease as the temperature increased was advantageous from the instrumental prospective. This TLC could not be used to monitor temperatures below 18° C. due to a strong decrease in reflectance below this temperature.

To ensure that no hysteresis effect, i.e. the observed reflectance was dependent on whether the temperature was increasing or decreasing, was being noted, data were collected using both TLCs with the temperature changing in both directions.

EXAMPLE II

Figure 3:
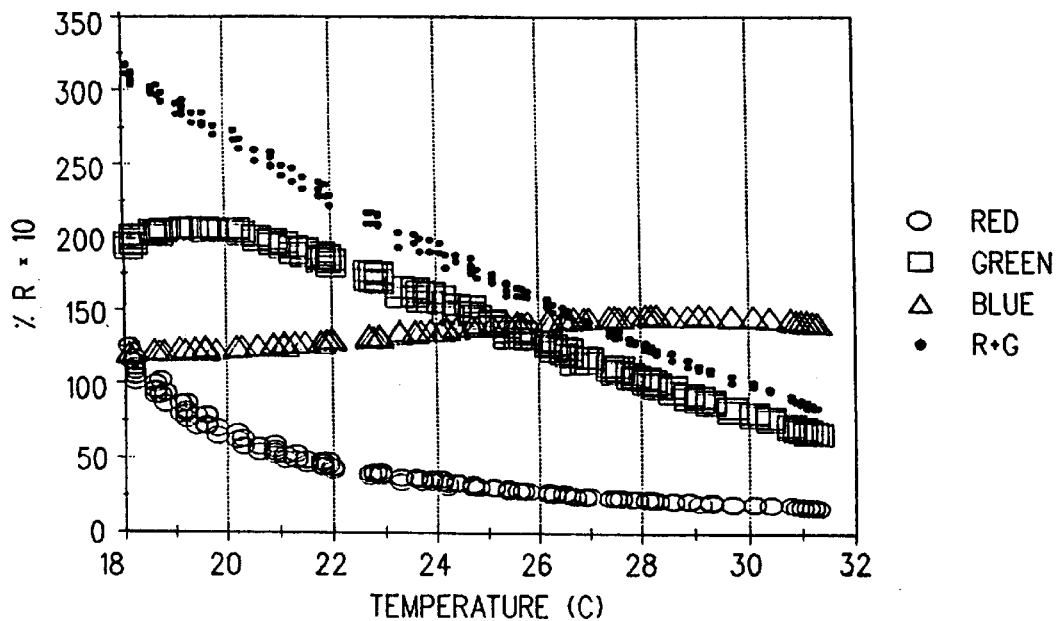
FIG. 3 illustrates the determination of temperature as a function of reflectance.

Additional data supporting the efficacy of using thermochromic liquid crystals as a method for determining temperature in conjunction with the spectrophotometric reading of an analysis strip is graphically represented by FIG. 3. The data were collected over a two day period in an environmental chamber which was cycled repeatedly between 18° C. and 30° C. with a constant relative humidity of 40%. Temperatures were recorded every 5 minutes from three different positions in relation to the TLC which was affixed to the spectrometer's specimen table. A CLINITEK® CT50 instrument was used in conjunction with a program that would initiate a reading every 5 minutes followed by collection of the TLC reflectance data along with the table, board and ambient temperatures. The table temperature came from an embedded probe at the tip position of the strip adjacent to the TLC position. The board temperature came from a temperature sensor which was on the circuit board near the readhead of the instrument. The ambient temperature came from a probe about 1 foot away from the instrument. Data were collected for over 31 hours (a total of 374 data points).

The signals obtained from each of the instruments IR, red, green and blue sensors were collected at each time point and plotted in FIG. 3. The % reflectance through the IR filter showed little or no change. The change in the red, green and blue filter signals as a function of temperature are shown in FIG. 3. The combined red and green signal was used since a greater signal change between 18 and 30° C. could be obtained. Using these data and a 2 polynomial regression fit through the data points, there was developed an equation by which the reflectance values through the red and green filters of the instrument could be converted to temperature. This equation is:

TLC temperature=38.068−0.0883 $(Rg+Rb)$+0.0000775 $(Rg+Rb)^2$ where Rg is the % reflectance through the green filter and Rb is the % reflectance through the red filter.

The relationship between the TLC reflectance response and the temperature to obtain the above equation was obtained by using an IBM compatible computer connected through a serial port connection to a Baytech Multiport controller. Output from a Cole-Palmer scanning thermocouple and output from a CLINITEK® CT50 instrument was matched through the Baytech controller. The output from the CT50 included reflectance readings through the red, green, blue and IR filters. The output from the scanning thermocouple included temperature readings from a probe approximately one foot from the instrument which was embedded in the table as described above and attached to the main circuit board close to the readhead of the instrument. Specialized software programmed in Visual Basic as used to initiate the 5 minute readings by the instrument and to obtain and match all of the datastreams.

Figure 4:
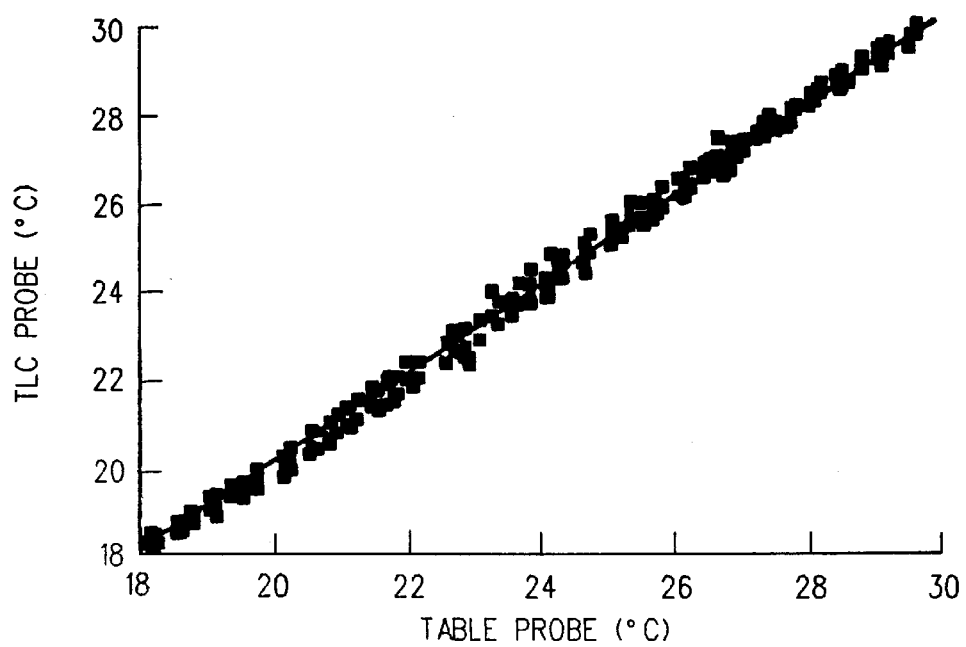
FIG. 4 illustrates the correlation of the TLC response with a probe.

The data set out in FIG. 4 represent the correlation of the TLC response (the summation of the green filter reflectance and the red filter reflectance) with that of the probe embedded in the table adjacent to the affixed TLC material. From FIG. 4 it can be determined that even under rapidly fluctuating temperatures there is good correlation between the temperatures recorded by the probe and those which are recorded by the TLC. Under these rapidly fluctuating environmental conditions the correlation between the TLC and the probe measuring the ambient air temperature were less robust. FIG. 3 correlates the TLC recorded temperature to that of the table temperature probe. The correlation shows a $R^2$ of 0.998 and a Sy.X (standard deviation of the line) of 0.203 where $R^2$ is the squared regression coefficient which shows the correlation between two measurements with the value of 1 demonstrating a perfect correlation with a value of 0 demonstrating no correlation at all between the two measurements. This indicates that within a 95% confidence limit, the correlation between the TLC and table probe is within half a degree.

For optimal results the TLC needs to be quite close to the test strip. There is typically a small temperature gradient within the instrument itself which, at least in a rapidly fluctuating temperature environment, would cause 1–3° C. temperature difference. Accordingly, the TLC is preferably placed on the test strip itself or on the specimen table near the strip as illustrated in FIG. 1.

EXAMPLE III

Figure 5:
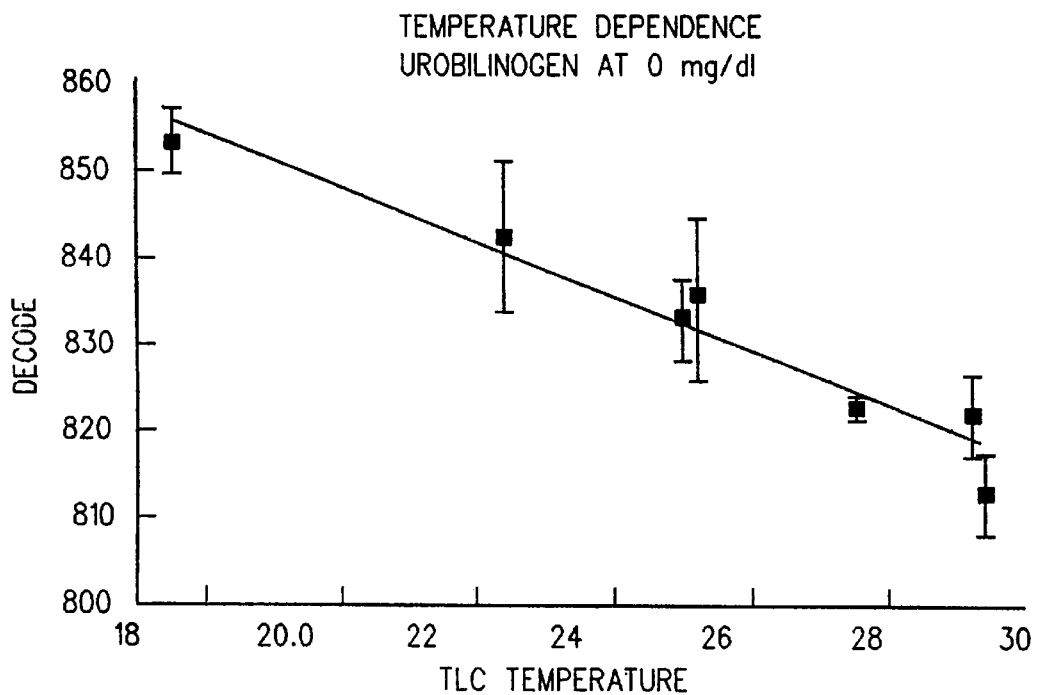
FIGS. 5 and 6 illustrate the sensitivity of reflectance measurements to temperature.
Figure 6:
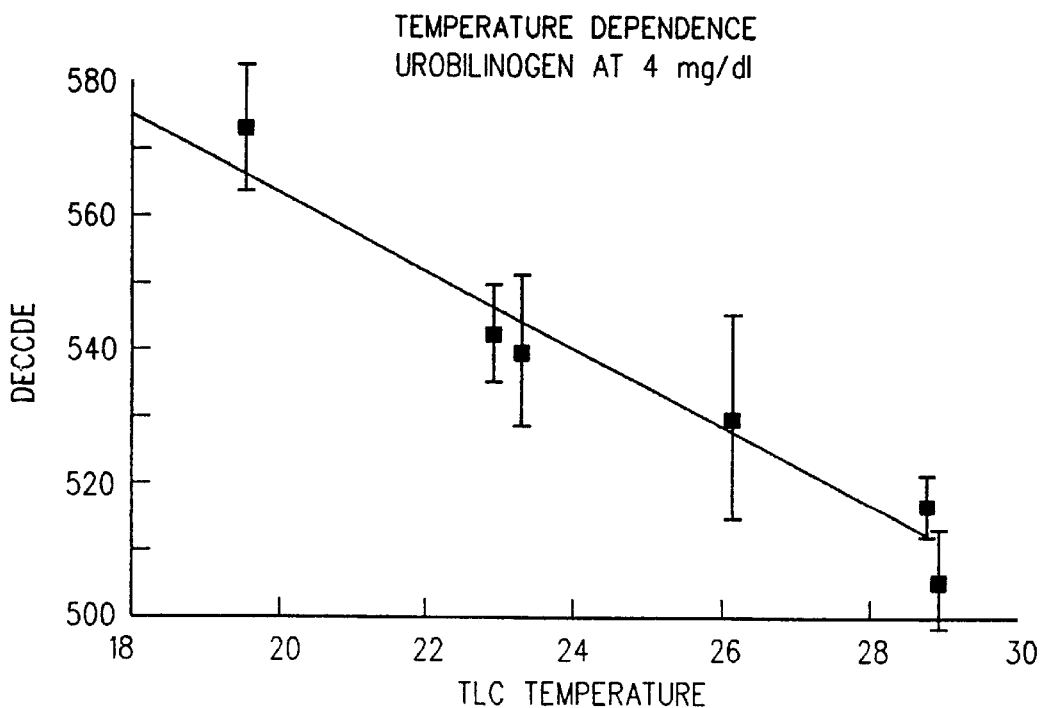

The temperature correcting ability of a reflectance read TLC is demonstrated by this example in which the urobilinogen pad of a MULTISTIX SG® strip was tested over several temperatures from 18 to 30° C. The results of this reagent pad are known to be sensitive to temperature as indicated by the product insert. The reflectance measurements are sensitive to temperatures as shown in FIGS. 5 and 6 using calibrated solutions containing 0 and 4 mg/dL urobilinogen in the fluid test sample. In all cases the decode, i.e. the algorithm result from the instrument, measurements (where decode is equal to the reflectance values obtained from green/IR filters of a CLINITEK® 50 spectrophotometer) show a negative response toward increases in temperature and appear to be linear. The factor change per degree change from 24° C. is calibrated by using:

$$\text{Delta}_{(factor\ change)} = 1 - \text{Decode}_{30C}/\text{Decode}_{24C}$$

Figure 7:
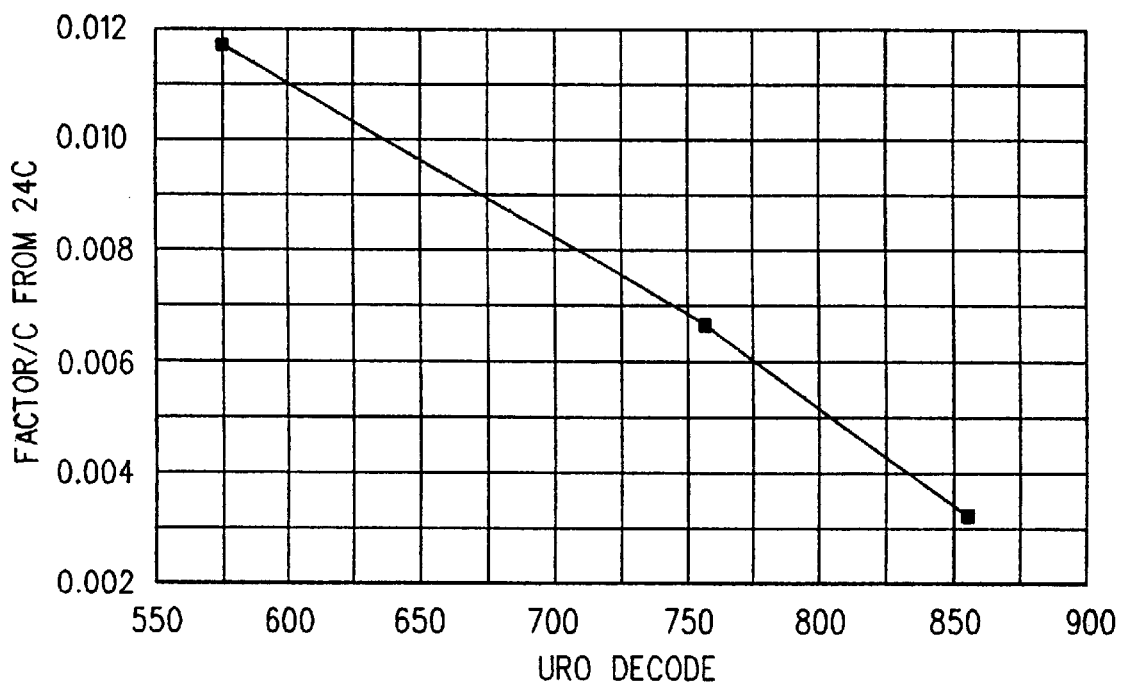
FIG. 7 illustrates the linear regression of the Delta (factor change) as a function of decode measurement.

This relationship is shown in FIG. 7 and is nearly linear. No difference was found when the factor difference was computed at a lower temperature. The above relationship was then used to calculate a corrected decode as a function of temperature using the following equation:

$$\text{Decode}_{Corrected} = \text{Decode}/\{1+(\text{Decode}*\text{Slope}+\text{Intercept})*(T_{actual-24})\}$$

where Slope=−2.94·10E-05 and Intercept =0.0287 wherein these values were calculated from the linear regression of the $\text{Delta}_{(factor\ change)}$ per °C. from 24° C. versus decode measurement in FIG. 7.

The results of this calculation are set out in Table 1.

TABLE 1

| Urobilinogen | DECODE, Uncorrected | | | DECODE, Corrected | | |
|---|---|---|---|---|---|---|
| (mg/dl.) | Max-Min | Avg. Value | SD | Max-Min | Avg. Value | SD |
| 0 | 41.4 | 831 | 12.9 | 8.6 | 837 | 2.8 |
| 1 | 56.7 | 727.6 | 19.7 | 15 | 731 | 4.2 |
| 4 | 66.9 | 540.1 | 23.5 | 18.9 | 540.9 | 6.3 |

As indicated by Table 1, a significant reduction in the error (in terms of standard deviation) on the order of about 4-fold is achieved by applying the TLC temperature correction to the data with no change in the average decode measurement. This demonstrates that TLC obtained temperature data can be used to significantly reduce the temperature induced error in cases where temperature control is not practical or available.

The present invention operates on the principle of measuring the reflectance of the TLC material through a reflectance meter. One or a combination of reflected wavelengths is chosen such that a unique value for a given temperature is obtained. As the TLC material's color changes from black→color→black with increasing temperature, it is desirable to limit the detected temperature range to an area where one or a combination of wavelength values give a numerical value. The reflectance of the TLC material is calibrated by relating these unique values to a given temperature and deriving an equation which allows the numerical calculation of temperature when only the reflectance of the TLC material is known. The temperature of the TLC material will be about the same as the temperature of the solid test material when the two are maintained in sufficiently close proximity. The accuracy of the temperature determining method may decrease as the TLC material and solid test material are separated by increasing distances. An example of such calibration is given by FIG. 4.

Temperature effects of the immunological or chemical reaction at given analyte levels are determined throughout the analyte range in which detection is desired. The chemical or immunological reactivity can be expressed in any form such as units, mg or any other form in which the data of FIGS. 5 and 6 are expressed as decode. A relationship between the decode value, which is a measure of the chemical or immunological reactivity, to that of temperature can be drawn from the relationships shown in FIGS. 5 and 6. As shown in FIG. 7, it is desirable to fixate the factor change in the decode value to the mid point of the desired temperature range in order to minimize bias in the calculations relating the decode to the temperature change.

Once the relationship has been established for a given lot of reagents and a given temperature range, the measured decode value is adjusted by the factor difference established for that decode value and the deviation of the temperature from the nominal value. This relationship can be any mathematical equation which allows the calculation of corrected decode from a measured decode and temperature measurement. In the present example, that relationship is described by a linear line with a slope of −2.94·11OE-05 and intercept of 0.0287. Accordingly, a measured decode value of 600 is corrected for temperature effects by software which uses the equation and computes the value of 563 for a corrected decode value of 562. An established relationship residing in the software between decode and analyte level is then used to provide the analyte concentration in the sample.

We claim:

1. In an assay for the presence and/or concentration of an analyte in a fluid test sample in which the presence and/or concentration of the analyte is determined by measuring a color change in a solid test material using a reflectance spectrometer after the test material has been contacted with the fluid test sample and wherein assay results vary with changes in temperature of the solid test material, the improvement which comprises using the reflectance spectrometer to determine the temperature of the solid test material by measuring the reflectance of a thermochromic liquid crystal in close proximity to the solid test material and correcting the results of the assay for deviation in temperature of the solid test material from a pre-selected nominal temperature.

2. The assay of claim 1 wherein the solid test material is a strip of an absorbant material having absorbed therein a reagent system which responds to the presence of the analyte in the fluid test sample with a visually detectable color change.

3. The assay of claim 1 wherein the thermochromic liquid crystal is of the cholesteric, chiral nematic or a combination thereof.

4. The assay of claim 1 wherein the color change in the solid test material is caused by an enzymatic reaction with the analyte which changes the color of a redox dye carried by the solid test material.

5. The assay of claim 1 wherein the color change in the solid test material is caused by the interaction of a ligand having a visually detectable marker with the analyte.

6. The assay of claim 1 wherein the analyte is urobilinogen and the test fluid test sample is urine.

7. The assay of claim 1 wherein the thermochromic liquid crystal is located on the solid test material.

8. The assay of claim 1 wherein the reflectance spectrometer has a specimen table for placement of the solid test material and the thermochromic liquid crystal and solid test material are located on the specimen table directly adjacent to each other.

9. The assay of claim 1, wherein the temperature of the solid test material is determined by:
   I) measuring the reflectance of the thermochromic liquid crystal through the reflectance spectrometer;
   ii) comparing the measured reflectance of the thermochromic liquid crystal to a first standard curve by:
      a) measuring a standard reflectance of the thermochromic liquid crystal at a plurality of standard temperatures to provide a first unique reflectance value for said plurality of standard temperatures;
      b) deriving an equation of the first standard curve which allows numerical calculation of a temperature of the thermochromic liquid crystal, when only the measured reflectance of the thermochromic liquid crystal is known; and
   iii) solving the equation to obtain the temperature of the solid test material.

10. The assay of claim 9, wherein the assay results of the analyte concentration in the fluid test sample are corrected for a change in temperature by:
   i) measuring the reflectance of the solid test material through the reflectance spectrometer;
   ii) comparing the measured reflectance of the solid test material to a second standard curve obtained by:
      a) measuring the reflectance of the solid test material at a plurality of standard temperatures and standard analyte concentrations to provide a second unique reflectance value for said plurality of standard temperatures and said standard analyte concentrations;
      b) deriving an equation of the second standard curve which allows numerical calculation of a correction for a change in temperature of the solid test material; and with the results of step iii) of claim 9,
   iii) solving the equation of the second standard curve to obtain temperature corrected assay results of the analyte concentration in said fluid test sample.

\* \* \* \* \*